United States Patent [19]

Cuca

[11] 4,385,049

[45] May 24, 1983

[54] STABLE HIGH INTERNAL PHASE RATIO TOPICAL EMULSIONS

[75] Inventor: Robert C. Cuca, Edwardsville, Ill.

[73] Assignee: K-V Pharmaceutical Company, St. Louis, Mo.

[21] Appl. No.: 263,024

[22] Filed: May 12, 1981

[51] Int. Cl.³ .................... A01N 61/02; A61K 47/00; A01N 25/22; A61K 31/00

[52] U.S. Cl. .................................. 424/167; 424/168; 424/169; 424/173

[58] Field of Search ................ 424/168, 173, 167, 169

[56] References Cited

U.S. PATENT DOCUMENTS

| | | | |
|---|---|---|---|
| 3,536,816 | 10/1970 | Kellner | 424/365 |
| 4,035,513 | 7/1977 | Kumano | 424/168 |
| 4,252,796 | 2/1981 | Yu et al. | 424/168 |
| 4,337,241 | 6/1982 | Ser et al. | 424/168 |

FOREIGN PATENT DOCUMENTS 9404  4/1980  European Pat. Off. .
1415528 11/1975  United Kingdom .

*Primary Examiner*—Delbert R. Phillips
*Assistant Examiner*—F. T. Moezie
*Attorney, Agent, or Firm*—Neal Kalishman

[57] ABSTRACT

Delivery systems for topical preparations which are commercially stable. The emulsions are water-in-oil in which the water phase comprises at least 75% of the emulsion by volume. The emulsifier is a nonionic oil soluble straight or branched chain ester or combination thereof composition having at least two hydrogen bonding sites per molecule.

9 Claims, No Drawings

STABLE HIGH INTERNAL PHASE RATIO TOPICAL EMULSIONS

BACKGROUND OF THE INVENTION

I. FIELD OF THE INVENTION

The present invention is directed to topical preparation systems which are high internal phase water-in-oil emulsions. Specifically, the invention is concerned with high internal phase water-in-oil emulsions which are commercially stable.

II. DESCRIPTION OF THE PRIOR ART

It has been found advantageous to formulate topical preparations in high internal phase ratio water-in-oil systems. Topical preparations include cosmetic and/or pharmaceutical products which are applied to external skin areas. By incorporating active agents desirable for topical use in high internal phase ratio water-in-oil emulsions, a number of advantages are obtained. Such advantages include the obtaining of an oil adherent system without utilizing high concentrations of oil.

A method of preparing a water-in-oil high internal phase ratio topical emulsion is described in United Kingdom Pat. No. 1,415,528 which is incorporated by reference herein. The emulsions disclosed in the patent do not display commercial stability. That is, they fail to remain emulsified for more than five freeze-thaw cycles. A freeze-thaw cycle is defined as the freezing of a sample of an emulsion at 14° F. for 24 hours and then allowing it to thaw at room temperature, 72° F., for 24 hours. Freeze-thaw cycles simulate conditions which may be encountered during transportation and/or storage of a product. For an emulsion to be commercially acceptable, it must survive at least five freeze-thaw cycles.

As discussed above, it has been possible to formulate water-in-oil high internal phase ratio topical emulsions which demonstrate limited noncommercial stability. The most commonly used emulsifier in these formulations is POE(2) oleyl ether which is oleic acid that has been oxyalkylated with two moles of ethylene oxide.

The present invention is advantageous in that it provides a nonlipoidal media in lipoidal media high internal phase ratio emulsion which is stable for extended periods, even at elevated temperatures. Further, the invention is advantageous since it provides a nonlipoidal media in lipoidal media high internal phase ratio emulsion which does not break or leak after five freeze-thaw cycles and remains on the skin for extended periods while being cosmetically acceptable.

SUMMARY OF THE INVENTION

The present invention provides delivery systems for topical preparations which comprise nonlipoidal media in lioidal media emulsions containing nonionic oil soluble straight or branched chain ester emulsifiers having at least two hydrogen bonding sites per molecule.

DESCRIPTION OF THE PREFERRED EMBODIMENTS

The present invention is directed to topical preparations incorporated into delivery systems which exhibit commercial stability. That is, they do not show phase separation or leaking of the internal phase after at least five freeze-thaw cycles. It has been discovered that this stability is attributable to the selection of a certain class of emulsifiers to form the emulsions. Also, the present invention is directed to preparations which do not wash off as easily as prior art preparations which are cosmetically acceptable since they do not feel waxy.

The emulsions of the inventions are comprised of lipoidal and nonlipoidal phases. The nonlipoidal phase comprises at least 75% of the emulsion and is the internal phase. This phase may comprise either water, glycerine, sorbitol, sugar syrups or combinations thereof. The internal phase may be multi-phasic and may be a solution, suspension, emulsion or combination thereof, and it may contain a portion of an active agent. Also, the internal phase may contain suspended solids, emulsions, extenders and dilutants, as well as colors, flavors and buffers.

The external phase is comprised of lipoidal media. This phase is the continuous phase of the systems. The term lipoidal pertains to any of a group of organic compounds comprising the neutral fats, fatty acids, waxes, steroids, petrolatum, phosphatides, fatty acid esters and mineral oils having the following common properties: insoluble in water, soluble in alcohol, ether, chloroform or other fat solvents, and which exhibit a greasy feel. Examples of oils suitable for use in these delivery systems are mineral oils with viscosities of 6.7 to 68.7 centistokes, preferably 6.7 to 42 centistokes, and vegetable oils illustrated by coconut, palm kernel, cocoa butter, cottonseed, peanut, olive, palm, sunflower seed, sesame, corn safflower, rape seed, soybean and fractionated liquid triglycerides of short chain (naturally derived) fatty acids. This external phase may also contain colors, flavors and buffers.

The systems may contain an independent active agent. Such an active agent may be any one of those which are approved for or used as topical applications in the treatment and/or prophylaxis of any disease diagnostic purposes, or cosmetic effect. Potential agents are normally well-known due to their common usage. The topical preparations of the invention have numerous uses, such as suntan lotions, moisturizing creams, rubdown emulsions, cleansing baby oil emulsions, wax cream, petrolatum creams, hair care creams, tooth polish, acne cream, tresaderm cream, hydrocortisone cream, antiperspirant, protective lotions, anti-inflamatory, including steroids and non-steroidal agents, analygesic agents, anti-fungal agents, anti-infective agents, emollients, agents for the treatment of psoriasis, antipruritics, and anti-acne agents, bleaching agents.

It has been found that cosmetic grade emulsifiers which are nonionic oil soluble straight or branched chain esters and have at least two hydrogen bonding sites per molecule produce the stable emulsions of the invention. Examples of such emulsifiers are polyglycerol oleate and glycerol monoisosterate. Polyglycerol oleate is produced by heating glycerol under a vacuum using a basic catalyst such as sodium acetate. A polyglycerol chain is formed which is then esterified with oleic acid. The product is partially dispersible in water having a hydrophylic-lipophylic balance (HLB) of approximately four. The glycerol monisosterate is made by esterifying glycerine with isosteric acid. This material has floculant-like properties when in contact with water caused by the incorporation of water into it.

As previously noted, it is believed that the two aforementioned emulsifiers form emulsions which are more stable than those of the prior art due to their being straight or branched chain esters, nonionic, oil soluble and having at least two hydrogen bonding sites per molecule. Emulsions utilizing these emulsifiers are able to withstand at least five freeze-thaw cycles. Emulsifiers which have cyclic rings and/or do not have at least two hydrogen bonding sites per molecule are ineffective in producing commercially stable emulsions.

The following examples illustrate the principles of the invention:

Method of Preparation: The active agent, and ingredients of the internal phase were mixed together at room temperature. The ingredients of the external phase were mixed together in a one-gallon vessel. The internal phase composition was slowly added to the external phase composition as the two phases were mixed together with a split disc stirrer at low shear until the desired viscosity was obtained.

The products described here may be prepared by continuous or batch processes. As in preparing conventional emulsions, shear force is applied to the system components by use of a homogenizer, mill, mixer, agitator, impingement surfaces, ultra-sound, shaking or vibration. Unlike conventional emulsions, the mixing shear should be at low levels in order to prevent destruction of the system by imparting excess energy. Temperature is not usually a critical factor in the preparation of the systems. The temperatures utilized will be dependent upon the final end product desired.

The products described here may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary depending upon the product produced as will the rate of flow of the two phase streams.

PROTECTIVE LOTION 1
(Initial Viscosity = 50K–100K CPS)

| Ingredients | % wt./wt. |
| --- | --- |
| Internal Phase | |
| Deionized Water | 79.15 |
| Sorbitol 70% Sln | 8.0 |
| Dowicil 200 | 0.1 |
| Silicone Fluid 200, 100 CS | 1.0 |
| External Phase | |
| Carnation Mineral Oil | 8.0 |
| Microcrystalline Wax | 0.5 |
| Polyglycerol Oleate | 3.25 |

PROTECTIVE LOTION 2
(Initial Viscosity = 60K–150K CPS)

| Ingredients | % wt./wt. |
| --- | --- |
| Internal Phase | |
| Deionized Water | 73.8982 |
| Sorbitol 70% Sln | 8.0 |
| Dowicil 200 | 0.1 |
| Silicone Fluid 200, 100 CS | 1.0 |
| External Phase | |
| Polyglycerol Oleate | 3.25 |
| Microcrystalline Wax | 0.5 |
| Fragrance | 0.1 |
| Red Dye #3 | .0018 |
| Carnation Mineral Oil | 8.0 |
| Active Phase | |
| TiO$_2$ | .15 |
| Talc | 5.0 |

PROTECTIVE LOTION 3
(Initial Viscosity = 250K–450K CPS)

| Ingredients | % wt./wt. |
| --- | --- |
| Internal Phase | |
| Deionized Water | 75.19 |
| Sorbitol 70% Sln | 8.0 |
| Dowicil 200 | 0.1 |
| Methylparaben | 0.14 |
| Silicone Fluid 200, 100 CS | 5.0 |
| External Phase | |
| Microcrystalline Wax | 0.5 |
| Gloria Mineral Oil | 5.0 |
| Glycerol Monoisosterate | 3.0 |
| Polyglycerol Oleate | 3.0 |
| Propylparaben | 0.03 |
| Fragrance | 0.025 |

BENZOCAINE 10%
(Initial Viscosity = 100K–400K CPS)

| Ingredients | % wt./wt. |
| --- | --- |
| Internal Phase | |
| Deionized Water | 69.3 |
| Glycerine | 8.0 |
| Benzyl Trimethyl Ammonium Hydrolyzed Animal Protein | 1.0 |
| Methylparaben | 0.15 |
| Propylparaben | 0.05 |
| Silicone Fluid 200, 100 CS | 1.0 |
| External Phase | |
| Carnation Mineral Oil | 7.0 |
| Polyglycerol Oleate | 3.0 |
| Microcrystalline Wax | 0.5 |
| Active Phase | |
| Benzocaine | 10.0 |

ANTIPERSPIRANT ROLL-ON
(Initial Viscosity = 28K CPS–50K CPS)

| Ingredients | % wt./wt. |
| --- | --- |
| Internal Phase | |
| Deionized Water | 38.5 |
| Sorbitol 70% Sln | 5.0 |
| Aluminum Chlorhydrate 50% Sln | 40.0 |
| Dowicil 200 | 0.1 |
| External Phase | |
| LMO #40 | 11.0 |
| Isopar C | 1.0 |
| Glycerol Monoisosterate | 4.0 |
| Fragrance | 0.3 |

BENZOYL PEROXIDE 5%
(Initial Viscosity = 200K–350K CPS)

| Ingredients | % wt./wt. |
| --- | --- |
| Internal Phase | |
| Deionized Water | 74.6 |
| Microcrystalline Wax | 8.0 |
| Dowicil 200 | 0.1 |
| CMC 7HF | 0.2 |
| Benzoyl Peroxide (Lucidol 70) | 7.1 |

-continued

| BENZOYL PEROXIDE 5% | |
|---|---|
| (Initial Viscosity = 200K–350K CPS) | |
| Ingredients | % wt./wt. |
| External Phase | |
| Carnation Mineral Oil | 5.0 |
| Glycerol Monoisosterate | 5.0 |

Each of the above compositions was subjected to a series of freeze-thaw cycles. The table following summarized the results.

| Composition | Average Minimum Number of Freeze-Thaw Cycles Prior to Breaking |
|---|---|
| Protective Lotion 1 | 10 |
| Protective Lotion 2 | 10 |
| Protective Lotion 3 | 10 |
| Benzocaine 10% | 10 |
| Antiperspirant Roll-On | 10 |
| Benzoyl Peroxide 5% | 10 |

The above compositions correspond to the compositions contained in the examples of this patent. A table summarizing the freeze-thaw stability of the products disclosed in the United Kingdom Pat. No. 1,415,528 are summarized below. The products were prepared in accordance with United Kingdom Pat. No. 1,415,528 and subjected to freeze-thaw cycles with both 5% and 8% sorbitol concentrations to insure that sorbitol did not effect stability.

| Example | Average Minimum Number of Freeze-Thaw Cycles Prior to Breaking |
|---|---|
| 11 | 0 |
| 11 (8% Sorbitol) | 0 |
| 12 | 0 |
| 13 | 0 |
| 16 | 1 |
| 16 (8% Sorbitol) | 1 |
| 20 | 1 |
| 21 | 2 |
| 23 | 0 |
| 24 | 5 |
| 26 | 5 |

As is apparent from the above results, the compositions of the prior art fail to achieve more than five freeze-thaw cycles. This compares with the compositions of the present invention which display stability through ten cycles.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Delivery systems for topical preparations which comprise nonlipoidal media in lipoidal media emulsions in which the nonlipoidal phase is at least 75% of the emulsion, the lipoidal phase containing nonionic oil soluble straight or branched chain ester or combinations thereof emulsifiers having at least two hydrogen bonding sites per molecule.

2. Delivery systems for topical preparations which comprise nonlipoidal media in lipoidal media emulsions in which the nonlipoidal phase is at least 75% of the emulsion, the lipoidal phase comprises an oil whose viscosity is between approximately 6.7 and 68.7 centristokes and contains nonionic oil soluble straight or branched chain ester or combinations thereof emulsifiers having at least two hydrogen bonding sites per molecule.

3. The delivery systems of claim 1 wherein said lipoidal media comprises mineral oils.

4. The delivery systems of claim 1 wherein said lipoidal media comprises vegetable oils.

5. The delivery systems of claim 1 wherein said nonlipoidal media comprises water.

6. The delivery systems of claim 1 wherein said nonlipoidal media comprises glycerine.

7. The delivery systems of claim 1 wherein said nonlipoidal media comprises sorbitol.

8. The delivery systems of claim 1 wherein said emulsifiers comprise polyglycerol oleate.

9. The delivery systems of claim 1 wherein said emulsifiers comprise glycerol monoisosterate.

* * * * *